US012642286B2

(12) United States Patent
Qin et al.

(10) Patent No.: US 12,642,286 B2
(45) Date of Patent: Jun. 2, 2026

(54) ENZYME COMPOSITIONS FOR PRODUCING CEREAL-BASED PRODUCT AND METHODS THEREOF

(71) Applicant: ZYMEBASE INC., Shanghai (CN)

(72) Inventors: Yulan Qin, Huzhou (CN); Xuerui Kou, Shanghai (CN); Yumei Wang, Shanghai (CN); Su Jiang, Shanghai (CN)

(73) Assignee: ZYMEBASE INC., Shanghai (CN)

( * ) Notice: Subject to any disclaimer, the term of this patent is extended or adjusted under 35 U.S.C. 154(b) by 574 days.

(21) Appl. No.: 18/161,093

(22) Filed: Jan. 30, 2023

(65) Prior Publication Data

US 2023/0165285 A1 Jun. 1, 2023

Related U.S. Application Data

(63) Continuation of application No. PCT/CN2020/106201, filed on Jul. 31, 2020.

(51) Int. Cl.
　*A23L 7/104* 　　　(2016.01)
　*C12N 9/24* 　　　(2006.01)

(52) U.S. Cl.
　CPC ............ *A23L 7/107* (2016.08); *C12N 9/2402* (2013.01); *C12Y 302/01001* (2013.01); *C12Y 302/01133* (2013.01)

(58) Field of Classification Search
　CPC ................. A23L 7/107; C12N 9/2402; C12Y 302/01001; C12Y 302/01133; C12Y 302/01002; C12Y 302/0106; C12Y 302/01098; C12P 19/00; C12P 19/02; C12P 19/04
　See application file for complete search history.

(56) References Cited

U.S. PATENT DOCUMENTS

| | | | |
|---|---|---|---|
| 4,996,063 A | 2/1991 | Inglett | |
| 6,190,708 B1 | 2/2001 | Triantafyllou | |
| 2007/0141688 A1 | 6/2007 | Henderson et al. | |
| 2008/0032373 A1 | 2/2008 | Bhargava et al. | |
| 2013/0266688 A1 | 10/2013 | Ortega et al. | |
| 2015/0111259 A1 | 4/2015 | Kleinhout et al. | |

FOREIGN PATENT DOCUMENTS

| | | | | |
|---|---|---|---|---|
| CN | 103260430 A | 8/2013 | | |
| CN | 104531805 A | 4/2015 | | |
| EP | 0289138 A2 | 11/1988 | | |
| EP | 0731646 B1 | 3/2001 | | |
| ES | 2359490 T3 * | 5/2011 | | |
| WO | 2000030457 A1 | 6/2000 | | |
| WO | 2009098229 A2 | 8/2009 | | |
| WO | 2010092149 A1 | 8/2010 | | |
| WO | 2012076052 A1 | 6/2012 | | |
| WO | WO-2014131861 A2 * | 9/2014 | .......... | C12N 9/2417 |
| WO | 2019229101 A1 | 12/2019 | | |

OTHER PUBLICATIONS

Cai, Yongjian et al., Study on Liquefying Technics of Isomaltooligosaccharides from Indica Rice Starch by Enzyme, Cereals & Oils, 29(1): 21-24, 2016.

Flávia Villas-Boas et al., Influence of Molecular Structure on The Susceptibility of Starch to α-amylase, Carbohydrate Research, 479 23-30, 2019.

First Office Action in Chinese Application No. 202080104613.3 mailed on Nov. 25, 2024, 23 pages.

International Search Report in PCT/CN2020/106201 mailed on Apr. 29, 2021, 5 pages.

Written Opinion in PCT/CN2020/106201 mailed on Apr. 29, 2021, 4 pages.

Rabi'atul Adawiyah Ahmad et al., Bioconversion of Starch to Maltooligosaccharides (MOS) by the Reaction of Maltogenic Amylase, Jurnal Teknologi (Sciences & Engineering), 2020, 7 pages.

Peter A. Sopade, Cereal processing and glycaemic response, International Journal of Food Science and Technology, 52: 22-37, 2017.

Pan, Sihui et al., Maltooligosaccharide-forming amylase: Characteristics, preparation, and application, Biotechnology Advances, 35: 619-632, 2017.

The Extended European Search Report in European Application No. 20947410.5 mailed on Jul. 26, 2023, 8 pages.

* cited by examiner

*Primary Examiner* — Erik Kashnikow
*Assistant Examiner* — Janice Y Silverman
(74) *Attorney, Agent, or Firm* — Metis IP LLC

(57) ABSTRACT

The present disclosure provides a method for preparing a cereal-based product. The method may include i) providing a cereal mixture including a cereal material and an aqueous medium. The method may include ii) treating the cereal mixture with an effective amount of an enzyme composition under a temperature to obtain a treated mixture, the enzyme composition including at least one malto-oligosaccharide forming amylase (MFAse). The method may further include iii) processing the treated mixture from step ii) to obtain the cereal-based product.

15 Claims, 7 Drawing Sheets

ENZYME COMPOSITIONS FOR PRODUCING CEREAL-BASED PRODUCT AND METHODS THEREOF

CROSS-REFERENCE TO RELATED APPLICATIONS

This application is a continuation of International Application No. PCT/CN2020/106201, filed on Jul. 31, 2020, the entire contents of which are hereby incorporated by reference.

TECHNICAL FIELD

The present disclosure generally relates to enzymatic reactions, and in particular, to enzyme compositions including at least one malto-oligosaccharide forming amylase (MFAse) and methods of producing a cereal-based product with the enzyme compositions.

BACKGROUND

Cereal-based food or drink are usually considered as healthy, since cereals contain dietary fibers (e.g., intact β-glucans) and are rich in nutrients such as starch, plant-based proteins, minerals, vitamins, etc. Cereal suspensions, such as oat milk, are a kind of cereal-based food or drink. The cereal suspensions are usually made by enzymatic hydrolysis of starch contained in cereals (e.g., oat, wheat, or maize). Amylases that degrade starch may be used for producing the cereal suspensions. α-amylases and β-amylases are commonly used to hydrolyze starch. An α-amylase can degrade starch but may yield a substantial amount of glucose, which may cause the cereal suspension to taste sweet. Moreover, the substantial amount of glucose may cause quickly increases in blood glucose levels in a human body. A β-amylase specifically generates maltose but is not effective enough to solubilize cereal starch, and thus there is usually a need to use a limited amount of α-amylase along with the β-amylase for producing cereal suspensions. As a result, a substantial amount of glucose may still be present in the cereal suspensions. Therefore, it is desirable to provide improved enzyme compositions for producing cereal-based products with a relatively low glucose content.

SUMMARY

According to an aspect of the present disclosure, a method for preparing a cereal-based product is provided. The method may include i) providing a cereal mixture including a cereal material and an aqueous medium. The method may include ii) treating the cereal mixture with an effective amount of an enzyme composition under a temperature to obtain a treated mixture, the enzyme composition including at least one malto-oligosaccharide forming amylase (MFAse). The method may further include iii) processing the treated mixture from step ii) to obtain the cereal-based product.

In some embodiments, the cereal material may include at least one of oat, quinoa, rye, sorghum, millet, maize, barley, wheat, triticale, fonio, buckwheat, rice, pea, chickpea, mung bean, faba bean, or soybean.

In some embodiments, the cereal mixture in step i) may include starch derived from a starch source.

In some embodiments, the starch source may include at least one of maize, millet, wheat, rice, pea, chickpea, mung bean, faba bean, soybean, cassava, potato, sweet potato, or yam.

In some embodiments, the aqueous medium may be water, milk, yoghurt, or juice.

In some embodiments, before step i), the cereal mixture may be prepared by at least one of a wet-milling process; a dry-milling process; a mixing process for mixing the cereal material and the aqueous medium; or a heating process.

In some embodiments, the at least one MFAse may include at least one of a maltose-forming amylase (G2-amylase), a maltotriose-forming amylase (G3-amylase), a maltotetraose-forming amylase (G4-amylase), a maltopentaose-forming amylase (G5-amylase), a maltohexaose-forming amylase (G6-amylase), or a maltoheptaose-forming amylase (G7-amylase).

In some embodiments, the at least one MFAse may include at least one of a maltose-forming amylase (G2-amylase), a maltotetraose-forming amylase (G4-amylase), or a maltohexaose-forming amylase (G6-amylase).

In some embodiments, the enzyme composition may further include at least one of an α-amylase, a β-amylase, or a γ-amylase.

In some embodiments, the temperature of step (ii) may be in a range of 40° C. to 75° C.

In some embodiments, the temperature of step (ii) may be in a range of 45° C. to 70° C.

In some embodiments, the temperature of step (ii) may be around 60° C.

In some embodiments, a termination condition for step (ii) may include at least one of a time period for treating the cereal mixture using the effective amount of the enzyme composition exceeds a time threshold; a viscosity of the cereal mixture is less than a viscosity threshold; or a starch level in the cereal mixture is less than a starch level threshold.

In some embodiments, the time threshold may be 72 hours.

In some embodiments, the time threshold may be 36 hours.

In some embodiments, the time threshold may be 2 hours.

In some embodiments, the viscosity threshold of the cereal mixture may be 80 mPa·s at a sheer rate of about 700 per second.

In some embodiments, the viscosity threshold of the cereal mixture may be 60 mPa·s at a sheer rate of about 700 per second.

In some embodiments, the viscosity threshold of the cereal mixture may be 40 mPa·s at a sheer rate of about 700 per second.

In some embodiments, the starch level threshold may be 60% of an original starch level in the cereal mixture.

In some embodiments, the starch level threshold may be 50% of an original starch level in the cereal mixture.

In some embodiments, the starch level threshold may be 35% of an original starch level in the cereal mixture.

In some embodiments, the effective amount of the enzyme composition may be 0.001%-1% of the cereal material by weight.

In some embodiments, the effective amount of the enzyme composition may be 0.005%-0.5% of the cereal material by weight.

In some embodiments, the effective amount of the enzyme composition may be 0.01%-0.1% of the cereal material by weight.

In some embodiments, processing the treated mixture may include inactivating one or more enzymes in the enzyme composition.

In some embodiments, the enzyme composition may be inactivated by heating the treated mixture to a temperature in a range of 75° C. to 100° C.

In some embodiments, processing the treated mixture further may include at least one of: a homogenizing process, a sterilization process, a refrigeration process, a concentrating process, a filtering process, or a drying process.

According to another aspect of the present disclosure, a cereal-based product prepared by the method is provided.

In some embodiments, the cereal-based product may include malto-oligosaccharides and maltodextrin units.

In some embodiments, a substantial amount of β-glucans and proteins included in the cereal material may be retained in the cereal-based product.

In some embodiments, a proportion of glucose in total soluble sugar in the cereal-based product may be less than 5% of the cereal-based product by weight.

In some embodiments, a proportion of glucose in total soluble sugar in the cereal-based product may be less than 3% of the cereal-based product by weight.

In some embodiments, the cereal-based product may be used as a food, a drink, an animal feed, a dietary supplement, or an additive.

In some embodiments, the cereal-based product may be in the form of a suspension, powder, granules, sheets, or blocks.

According to a further aspect of the present disclosure, a use of an enzyme composition for preparing a cereal-based product from a cereal material is provided. The enzyme composition may include at least one malto-oligosaccharide forming amylase (MFAse), and preparing the cereal-based product may include i) providing a cereal mixture including the cereal material and an aqueous medium; ii) treating the cereal mixture with an effective amount of the enzyme composition under a temperature to obtain a treated mixture; and iii) processing the treated mixture from step ii) to obtain the cereal-based product.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein.

4

Figure 3:
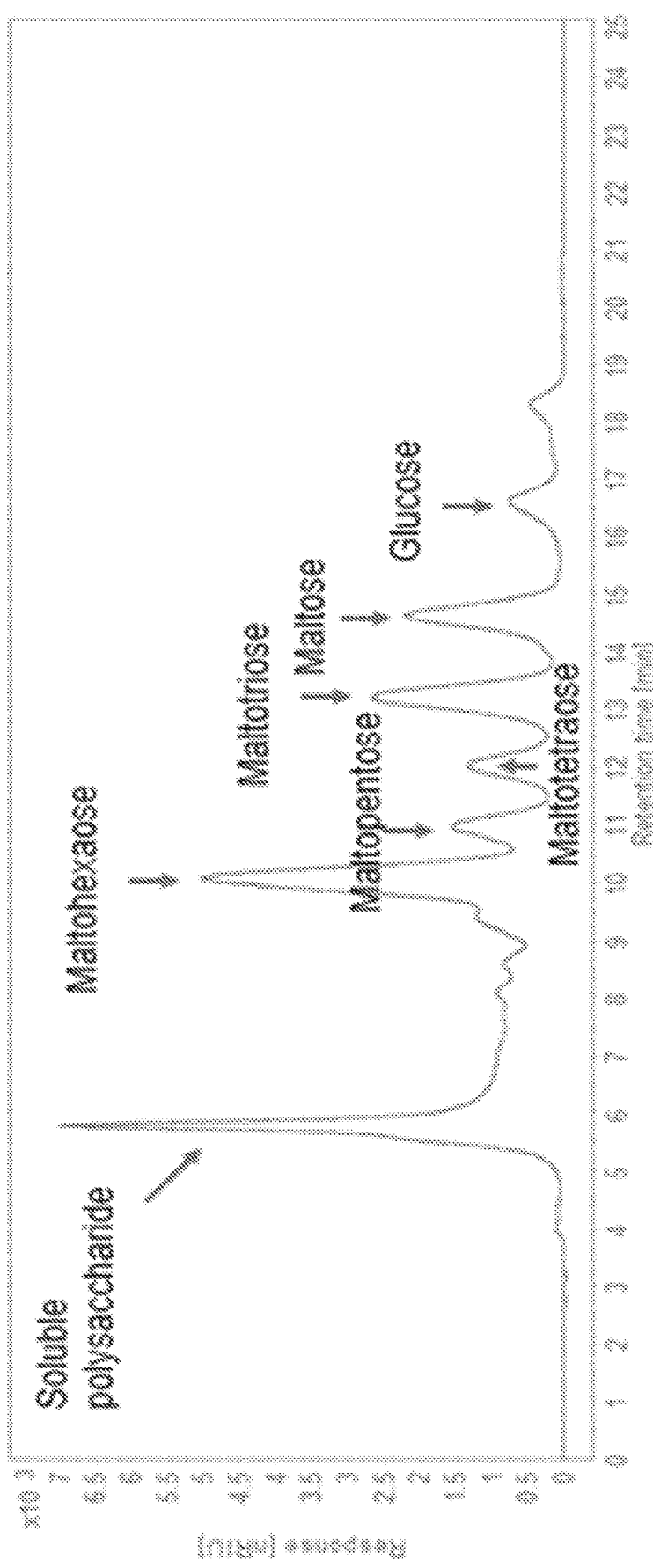
Figure 4:
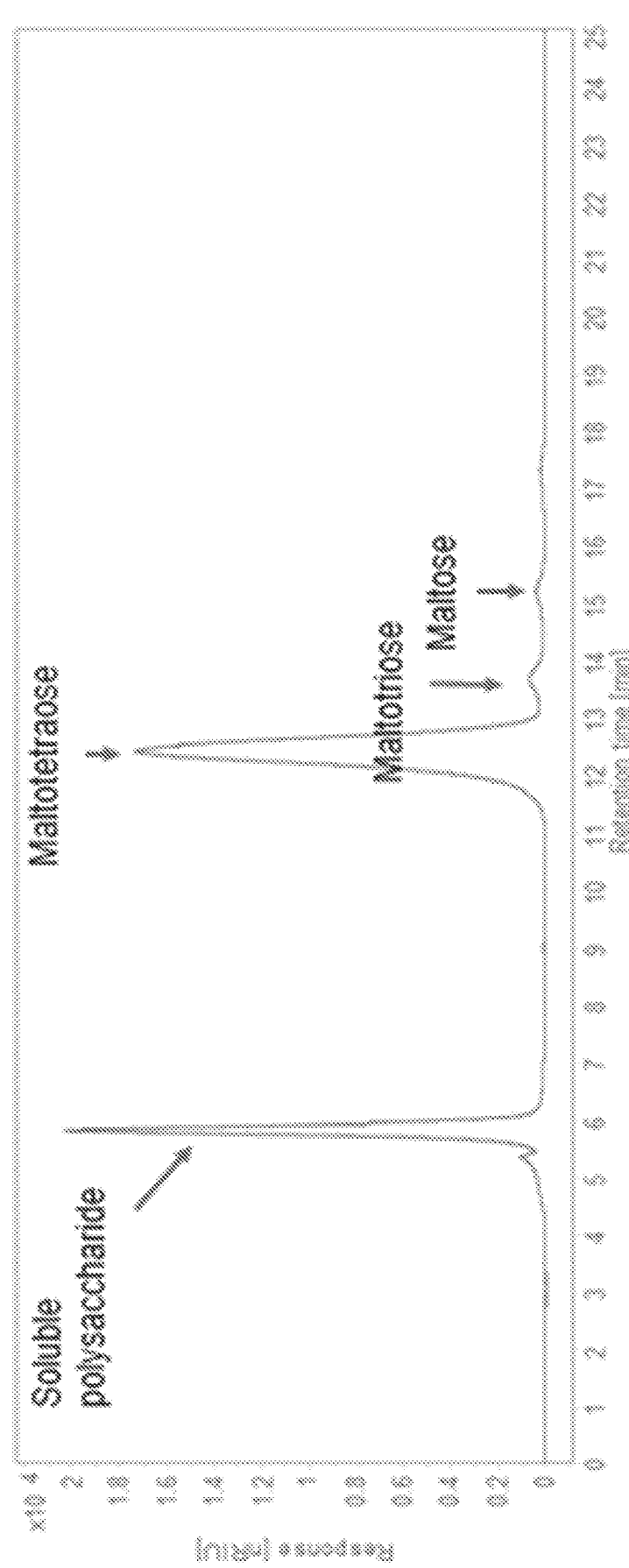
Figure 5:
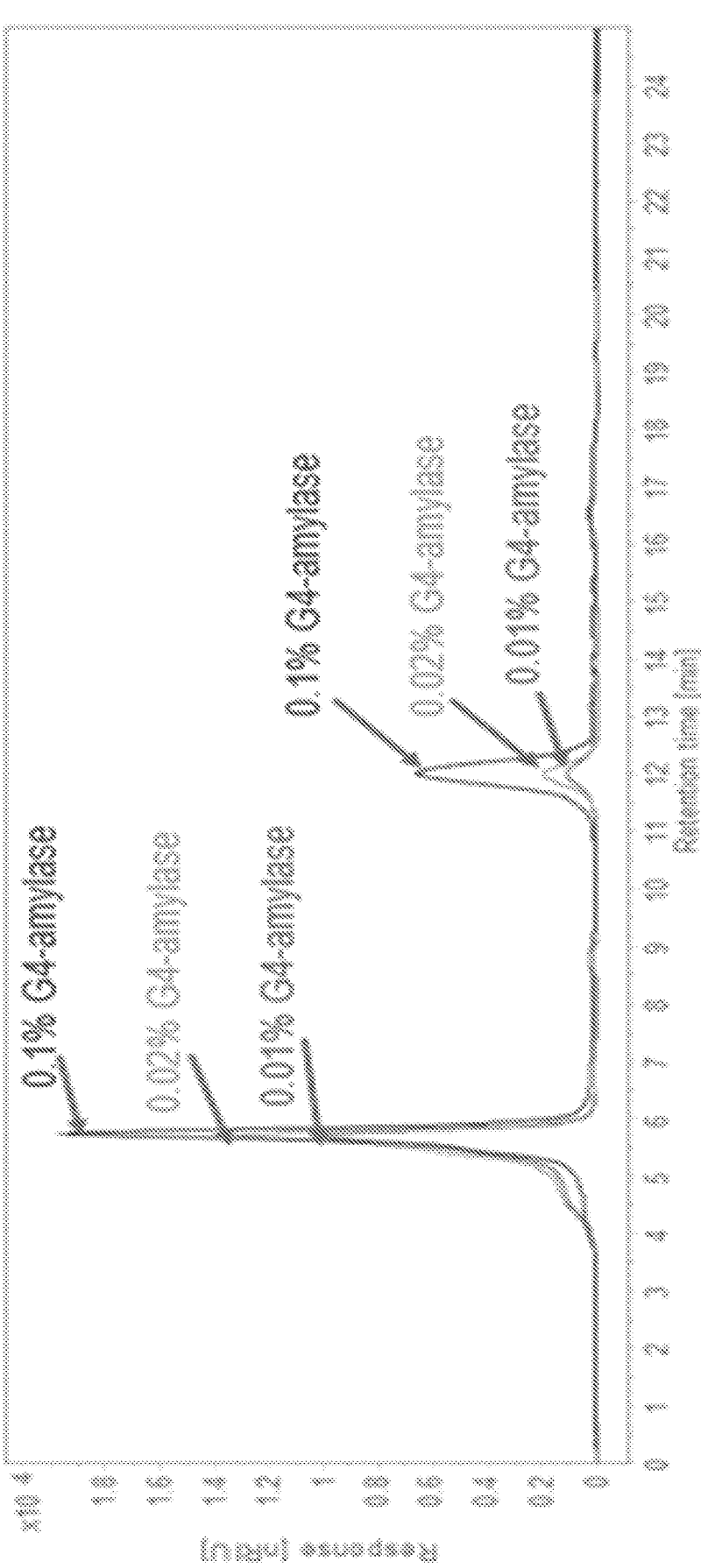
Figure 6:
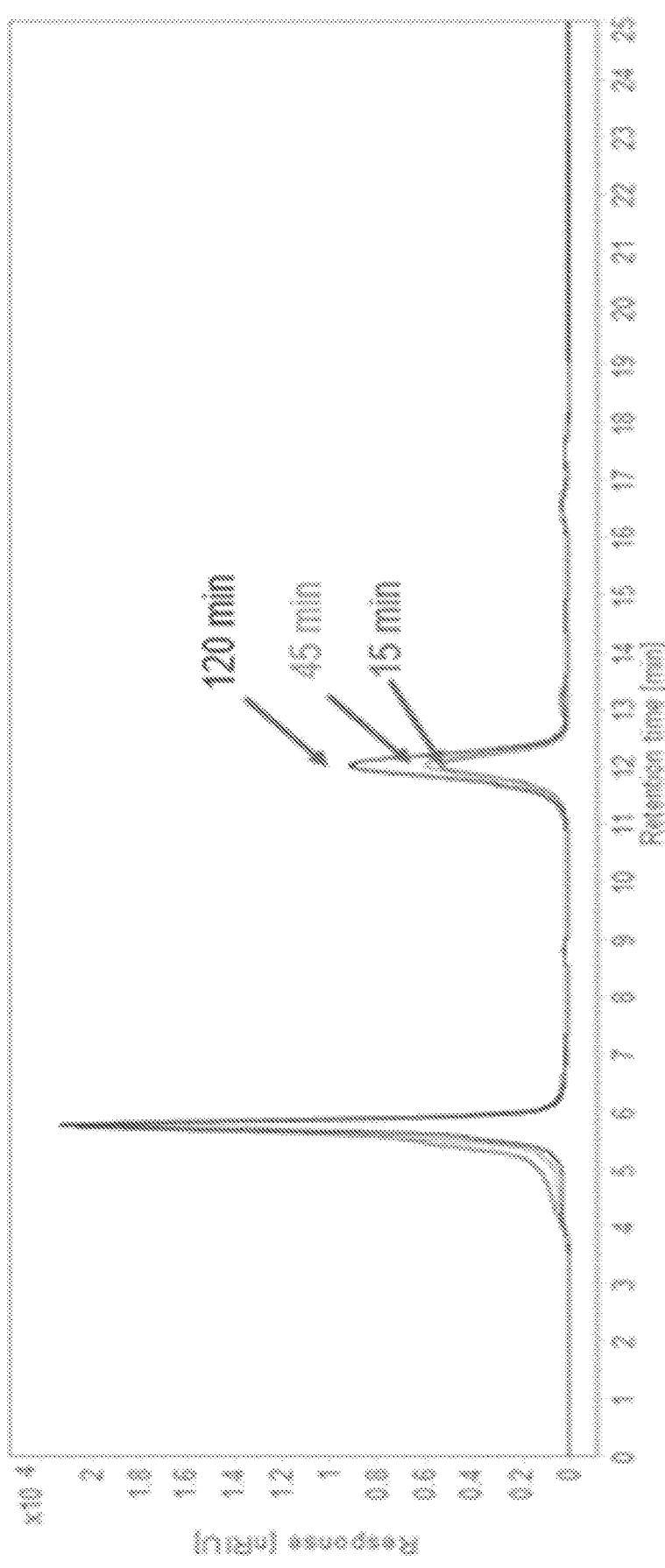
Figure 7:
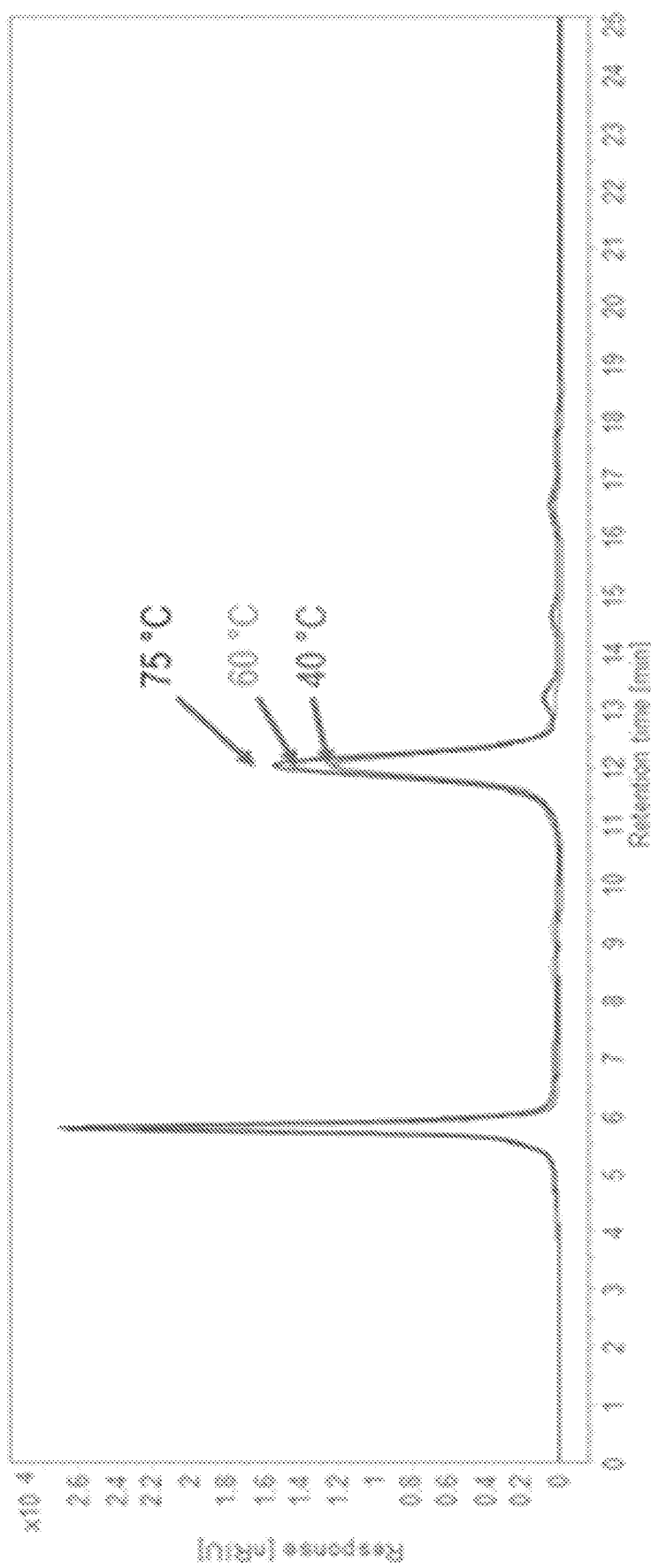

FIG. 3 is an analytical graph illustrating a result of soluble carbohydrate analysis of a cereal suspension treated by a G6-amylase according to some embodiments of the present disclosure;

FIG. 4 is an analytical graph illustrating a result of soluble carbohydrate analysis of a cereal suspension treated by the G4-amylase according to some embodiments of the present disclosure;

FIG. 5 is an analytical graph illustrating a result of soluble carbohydrate analysis of cereal suspensions treated by different dosages of the G4-amylase according to some embodiments of the present disclosure;

FIG. 6 is an analytical graph illustrating a result of soluble carbohydrate analysis of the suspensions treated by the G4-amylase for different reaction time according to some embodiments of the present disclosure; and FIG. 7 is an analytical graph illustrating a result of soluble carbohydrate analysis of the suspensions treated by the G4-amylase at different reaction temperatures.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) is for the purpose of illustration and description only and are not intended to limit the scope of the present disclosure. It is understood that the drawings are not to scale.

The present disclosure provides a use of an enzyme composition for preparing a cereal-based product. In some embodiments, the enzyme composition may include at least one malto-oligosaccharide forming amylase (MFAse). In some embodiments, the at least one MFAse may include a maltose-forming amylase (G2-amylase), a maltotriose-forming amylase (G3-amylase), a maltotetraose-forming amylase (G4-amylase), a maltopentaose-forming amylase (G5-amylase), a maltohexaose-forming amylase (G6-amylase), a maltoheptaose-forming amylase (G7-amylase), or the like, or any combination thereof.

The present disclosure further provides a method for preparing the cereal-based product with the enzyme composition. For example, the method for preparing the cereal-based product may include i) providing a cereal mixture including a cereal material and an aqueous medium; ii) treating the cereal mixture with an effective amount of an enzyme composition under a temperature to obtain a treated mixture; and iii) processing the treated mixture from step ii) to obtain the cereal-based product.

The present disclosure further provides a cereal-based product prepared by the above method. A substantial amount of non-starch ingredients included in the cereal material, such as β-glucans and proteins, is retained in the cereal-based product, which enables the cereal-based product to taste and smell like natural cereal materials. Moreover, a proportion of glucose in total soluble sugar in the cereal-based product may be less than 5% of the cereal-based product by weight. The prepared cereal-based product may achieve characteristics of a relatively low sweetness level, a relatively low glycemic index (GI), and a relatively low osmotic pressure. The low osmotic pressure may make it easier for the intestine and/or stomach to absorb the nutrients in the cereal-based product. Thus, the prepared cereal-based product may be healthy food or drink for humans or animals. The cereal-based product may also be used as an additive or a dietary supplement. Moreover, since the cereal-based product contains a substantial amount of proteins, the cereal-based product may be used as an alternative to milk, especially for lactose-intolerant people.

As used herein, the term "cereal material" of the present disclosure refers to material obtained from cereals. Exemplary cereal material may include but not limited to oat, quinoa, rye, sorghum, millet, maize, barley, wheat, triticale, fonio, buckwheat, rice, pea, chickpea, mung bean, faba bean, soybean, or the like, or a mixture thereof. The cereal material may be provided in various forms, such as powder, granules, sheets, or blocks. The cereal material may contain nutrients such as dietary fibers (e.g., intact β-glucans), starch, plant-based proteins, minerals, vitamins, etc.

Starch (also referred to as amylum) is a polymeric carbohydrate consisting of numerous glucose units joined by glycosidic bonds. Starch is one of the most important dietary carbohydrates that provide energy for metabolic activities for humans and animals. A variety of plants produce starch and use starch for energy storage. Cereal grains and root vegetables are common sources of starch. For instance, oats usually contains 50%-60% by weight; rice usually contains 62%-86% starch by weight; wheat usually contains 57%-75% by weight; maize usually contains 65%-72% by weight; and potato usually contains 12%-14% by weight.

As used herein, the term "MFAse" refers to a family of enzymes that specifically produce malto-oligosaccharides composed of multiple α-D-glucopyranosyl units (e.g., 2-10 α-D-glucopyranosyl units) by degrading starch. The MFAses can be classified based on the specific degree of polymerization (DP) of the produced malto-oligosaccharides. For instance, the MFAses may include maltose-forming amylase (G2-amylase; EC 3.2.1.133), maltotetraose-forming amylase (G4-amylase; EC 3.2.1.60), maltohexaose-forming amylase (G6-amylase; EC 3.2.1.98), and other amylases that can specifically produce maltooligosaccharides from starch. Exemplary other amylases may include but not limited to maltotriose-forming amylase (G3-amylase; EC 3.2.1.116), maltopentaose-forming amylase (G5-amylase; EC 3.2.1.-), maltohexaose and maltoheptaose-forming amylase (G7-amylase, EC 3.2.1.98), etc.

According to an aspect of the present disclosure, a method of preparing a cereal-based product is provided. In some embodiments, the method may include i) providing a cereal mixture including a cereal material and an aqueous medium; ii) treating the cereal mixture with an effective amount of an enzyme composition under a temperature to obtain a treated mixture, the enzyme composition including at least one malto-oligosaccharide forming amylase (MFAse); and iii) processing the treated mixture from step ii) to obtain the cereal-based product.

In some embodiments, the cereal material may include at least one of oat, quinoa, rye, sorghum, millet, maize, barley, wheat, triticale, fonio, buckwheat, rice, pea, chickpea, mung bean, faba bean, soybean, or a mixture thereof. The cereal material may include various nutrients such as dietary fibers, saccharides, starch, proteins, minerals, etc. Thus, the cereal material can be considered as a source of healthy food for human beings and/or animals. In some embodiments, the cereal material may be a material derived from the forementioned cereals. For instance, the cereal material may include starch derived from the cereals. The cereal material may be provided in various forms, such as powder, granules, sheets, or blocks.

The cereal mixture refers to a mixture of the cereal material and the aqueous medium. The aqueous medium refers to an aqueous liquid. The aqueous medium may include but not limited to water, milk, yoghurt, juice, wine (such as beer, liquor, champagne), or a mixture thereof. In some embodiments, the cereal mixture may include substances that are insoluble in the aqueous medium. For example, the cereal mixture may be provided in the form of a suspension, and the cereal mixture may also be referred to as a "cereal suspension"). As another example, the cereal mixture may be a paste, a slurry, or any other form of solid-liquid mixtures. In some embodiments, the cereal material, such as starch derived from cereals, may be fully solubilized in the aqueous medium. In some embodiments, the aqueous medium may be used to facilitate a reaction of one or more components of the cereal material (e.g., starch) with one or more enzymes (e.g., MFAses). In some embodiments, the aqueous medium, such as yoghurt, may increase the flavor of the cereal-based product.

In some embodiments, one or more pre-processing operations may be performed on the cereal material for preparing the cereal mixture. The one or more pre-processing operations may include a dehulling process for separating grains from hulls, a cleaning process, a crushing process, or the like, or any combination thereof. The material mixture may be prepared by a wet milling process, a dry milling process, a mixing process, a heating process, or the like, or any combination thereof. The wet-milling process refers to a process of milling the cereal material with the presence of the aqueous medium. The dry-milling process refers to a process of milling the cereal material without the aqueous medium. The heating process refers to a process of heating the cereal mixture for a time period (e.g., to cause the starch contained in the cereal material to gelatinize). The mixing process refers to a process of mixing the cereal material with the aqueous medium. For example, the cereal material, such as oat, may be dry-milled to produce small fragments, and the small fragments may be mixed with the aqueous medium to obtain a preliminary mixture. The preliminary mixture may be heated to obtain the cereal mixture. As another example, the oat may be mixed in the aqueous medium to obtain a preliminary mixture, and the preliminary mixture may be heated for a certain time period (e.g., for 20-40 minutes). After heating, the preliminary mixture may be wet-milled to produce the cereal mixture. In some embodiments, additional substances (such as additional starch, additional fiber, additional proteins, etc.) may be mixed with the cereal material and the aqueous medium. For example, the additional starch may derive from a starch source. The starch source may be cereals or other starch-containing materials. Exemplary starch sources may include maize, millet, wheat, rice, pea, chickpea, mung bean, faba bean, soybean, cassava, potato, sweet potato, yam, or the like, or a combination thereof.

In some embodiments, a ratio of the cereal material to the aqueous medium may be in a range of about 3% to 20% (weight/volume, w/v). In some embodiments, the ratio of the cereal material to the aqueous medium may be in a range of about 5% to 15% (w/v). In some embodiments, a ratio of the cereal material to the aqueous medium may be in a range of about 5%, 10%, 15%, etc.

In step ii), the cereal mixture may be treated with an effective amount of an enzyme composition under a temperature to obtain a treated mixture. The enzyme composition refers to a composition including one or more enzymes that can degrade starch.

In some embodiments, the enzyme composition may include at least one malto-oligosaccharide forming amylase (MFA or MFAse). The at least one MFAse may include a maltose-forming amylase (G2-amylase), a maltotriose-forming amylase (G3-amylase), a maltotetraose-forming amylase (G4-amylase), a maltopentaose-forming amylase (G5-amylase), a maltohexaose-forming amylase (G6-amylase), a maltoheptaose-forming amylase (G7-amylase), or the like, or any combination thereof. In some embodiments, the MFAse may derive from microbes. For instance, the MFAse may be derived from fungi (e.g., *Cryptococcus* species (sp.), *Fusicoccum* sp., *Scytalidium thermophilum*), bacteria (e.g., *Bacillus* sp., *Corallococcus* sp.). Merely by way of example, a specific G2-amylase may include a maltogenic *Bacillus stearothermophilus* amylase. A specific G3-amylase may include maltotriose forming *Streptomyces griseus* amylase. A specific G4-amylase may include malto-tetraose forming amylase from *Pseudomonas stutzeri* or *Pseudomonas saccharophila*. A specific G6-amylase may include maltohexaose forming *Aerobacter aerogenes* amylase. As another example, the at least one MFAse may be artificially synthesized through genetic engineering techniques.

In some embodiments, the enzyme composition may contain a single enzyme selected from the MFAses. For example, the enzyme composition may include a G2-amylase (see, e.g., Example 1), a G4-amylase (see, e.g., Example 2), or a G6-amylase (see, e.g., Example 3). The process of treating the cereal mixture using the single enzyme may be controlled or manipulated efficiently. It may be convenient to control the content of sugar (e.g., malto-oligosaccharide and glucose), the viscosity of the cereal mixture, and/or other parameters during the process of treating the cereal mixture.

In some embodiments, the enzyme composition may contain multiple enzymes selected from the MFAses. Merely by way of example, the enzyme composition may include the G2-amylase and the G4-amylase. As another example, the enzyme composition may include the G4-amylase and the G6-amylase. As yet another example, the enzyme composition may include the G2-amylase, the G4-amylase, and the G6-amylase.

Optionally, apart from the at least one MFAse, the enzyme composition may further include one or more other starch-degrading enzymes, such as an α-amylase, a β-amylase, a γ-amylase, a pullulanase, or the like, or any combination thereof. α-amylases are endo-action enzymes that hydrolyze internal α-1,4 linkages of glucose polymers by endo-attack with retention of the anomeric configuration. β-amylases are exo-amylases, which catalyze the successive removal of maltose from the non-reducing ends of the glucose polymers with inversion of the anomeric configuration. The use of multiple starch degrading enzymes may increase the efficiency of the degradation of starch in the process of treating the cereal mixture. In some embodiments, the enzyme composition may further include other types of enzymes, which are not limited by the present disclosure. For example, the enzyme composition may further include a glucose isomerase that converts glucose into d-fructose.

In some embodiments, the temperature of step ii) may be in a range of 35° C. to 80° C. In some embodiments, the temperature of step ii) may be in a range of 40° C. to 75° C. In some embodiments, the temperature of step ii) may be in a range of 45° C. to 70° C. In some embodiments, the temperature of step ii) may be in a range of 50° C. to 65° C. For example, the temperature of step ii) may be around 55° C., 60° C., 65° C., etc. As used herein, the term "around" means there may be an acceptable data fluctuation within a certain range (e.g., within a range of ±5% or ±3%). For instance, "around 60° C." may indicate that there may be a deviation of ±1-2° C. of the temperature of 60° C. when implementing the methods provided by the present disclosure.

To control the enzymatic reaction in the process of treating the cereal mixture, a termination condition may be set. In some embodiments, the termination condition for step (ii) may include a time period for treating the cereal mixture using the effective amount of the enzyme composition exceeds a time threshold; a viscosity of the cereal mixture is less than or equal to a viscosity threshold; a starch level in the cereal mixture is less than or equal to a starch level threshold, or other termination condition, or any combination thereof.

In some embodiments, the time threshold may be around 72 hours. In some embodiments, the time threshold may be around 36 hours. In some embodiments, the time threshold may be around 4 hours. In some embodiments, the time threshold may be around 2 hours. In some embodiments, the time threshold may be around 1 hour. In some embodiments, the time threshold may be around 15 minutes, 30 minutes, 45 minutes, etc.

In some embodiments, one or more parameters may be measured during the process of treating the cereal mixture with the enzyme composition (i.e., step ii)). For example, the one or more parameters may include the viscosity of the cereal mixture and/or the starch level. Additionally or alternatively, the one or more parameters may include the pH of the cereal mixture, the temperature of the cereal mixture, a glucose level, a malto-oligosaccharide level, or the like, or any combination thereof. In some embodiments, values of the one or more parameters may be controlled within a suitable range. For example, the pH of the cereal mixture may be controlled within a range that is suitable for the enzymatic reaction between the enzyme composition and the cereal mixture, such as 4.9 to 12, 5-8, 6-7, etc. In some embodiments, when a value of the viscosity is less than or equal to the viscosity threshold, step ii) may be terminated. Additionally or alternatively, when a value of the starch level is less than or equal to the starch level threshold, step ii) may be terminated. For instance, the viscosity threshold may be 80 mPa·s at a sheer rate of about 700 per second, 60 mPa·s at a sheer rate of about 700 per second, 40 mPa·s at a sheer rate of about 700 per second, 40 mPa·s at a sheer rate of about 700 per second, 30 mPa·s at a sheer rate of about 700 per second, etc. In some embodiments, the starch level threshold may be in a range of 65%-30% of the original starch level in the cereal mixture. The original starch level refers to a level of starch content in the cereal mixture before treating the cereal mixture with the enzyme composition. For example, The starch level threshold may be 60%, 50%, 35%, 30%, etc., of the original starch level in the cereal mixture. The starch level in the cereal mixture may be determined by an Iodine colorimetry method, a reducing sugar determination method, etc.

In some embodiments, the effective amount of the enzyme composition used in step ii) may be 0.001%-1% of the cereal material by weight. In some embodiments, the effective amount of the enzyme composition may be 0.005%-0.5% of the cereal material by weight. In some embodiments, the effective amount of the enzyme composition may be 0.01%-0.1% of the cereal material by weight. For example, the effective amount of the enzyme composition may be around 0.01%, 0.02%, 0.05%, 0.1%, or the like, of the cereal material by weight.

In some embodiments, the method may further include processing the treated mixture from step ii) to obtain the cereal-based product. For example, processing the treated mixture may include a process of inactivating one or more enzymes in the enzyme composition. Optionally, processing the treated mixture may further include a homogenizing process, a sterilization process, a refrigeration process, a concentrating process, a filtering process, a drying process, or the like, or any combination thereof. One or more of the fore-mentioned processes for processing the treated mixture may be performed in any order or concurrently. Different forms of the cereal-based product may be obtained with different processes performed on the treated mixture. The cereal-based product may be in the form of a suspension, an emulsion, powder, granules, sheets, or blocks. For example, if a drying process is performed on the treated mixture, the cereal-based product may be a solid product. The filtering process may be intended to remove insoluble substances with a relatively large size.

The enzyme(s) in the treated mixture may be inactivated under extreme temperatures and/or pH values for a certain time period (e.g., 5 minutes, 10 minutes). In some embodiments, the temperature for inactivating the MFAse(s) may be in a range of 70° C. to 100° C. In some embodiments, the temperature for inactivating the MFAse(s) may be in a range of 75° C. to 95° C. In some embodiments, the temperature for inactivating the MFAse(s) may be in a range of 80° C. to 95° C. In some embodiments, the temperature for inactivating the MFAse(s) may be in a range of 85° C. to 95° C. For example, the temperature for inactivating the MFAse(s) may be around 95° C., 92° C., 90° C., etc. It should be noted that other methods for inactivating the enzyme(s) in the treated mixture may also be implemented in the methods for preparing the cereal-based product, which is not limited by the present disclosure. In some embodiments, the pH for inactivating the enzyme(s) in the treated mixture may be 2, 3, 13, 14, etc.

The homogenizing process is intended to cause substances in the treated mixture to distribute uniformly throughout the aqueous medium. For example, the homogenizing process may be accomplished by reducing the size of insoluble substances in the treated mixture using extruders, hammerm ills, colloid mills, etc. Thus, the cereal-based product, such as a cereal suspension, may be homogenous and stable.

The sterilization process refers to a process that removes, kills, or inactivates microorganisms (such as fungi, bacteria, viruses, spores, plasmodium, etc.) and other biological agents like prions present in the treated mixture. The sterilization process may be achieved through various means, including heating, irradiation, providing a relatively high pressure, sterile filtration, etc. For example, the treated mixture may be sterilized by heating the treated mixture for a certain time period. In some embodiments, heating the treated mixture may achieve both the purpose of inactivating the enzyme(s) in the treated mixture and the purpose of sterilization.

The refrigeration process refers to a process of decreasing the temperature of the treated mixture, or holding the temperature of the treated mixture at a relatively low level for storage. For example, the treated mixture may be stored in a refrigerator.

The concentrating process refers to a process of increasing the concentration of the soluble substances and/or insoluble substances in the treated mixture by evaporation. An exemplary concentrating process may include but not limited to an evaporation concentrating process, a freeze concentrating process, a membrane concentrating process, etc.

The drying process refers to a process of removing water or other liquid in the treated mixture. Exemplary drying process may include but not limited to stream drying, vacuum drying, drum drying, spray drying, freeze-drying, etc.

According to another aspect of the present disclosure, a cereal-based product prepared by the above methods is provided. In some embodiments, preparing the cereal-based product may include i) providing a cereal mixture including the cereal material and an aqueous medium; ii) treating the cereal mixture with an effective amount of the enzyme composition under a temperature to obtain a treated mixture; and iii) processing the treated mixture from step ii) to obtain the cereal-based product. More description about the method of preparing a cereal-based product may be found elsewhere in the present disclosure, and is not repeated herein.

The cereal-based product may include a substantial content of fibers (e.g., β-glucans), proteins, malto-oligosaccharides, maltodextrin units, or the like, or a combination thereof. The fibers, β-glucans, and/or proteins contained in the cereal material may be retained in the cereal-based product. The β-glucans may include a group of β-D-glucose polysaccharides naturally occurring in cell walls of the cereal material. The β-glucans can improve immunity, gut health, cholesterol levels, and reduce the risk of a heart disease. Moreover, the content of glucose in the cereal-based product may be relatively low. For instance, a proportion of glucose in total soluble sugar in the cereal-based product by weight may be less than 5%, 3%, 2%, 1%, etc. Therefore, the cereal-based product may be healthy food or drink for humans and/or animals. For instance, the cereal-based product may include but not limited to cereal-based milk, cereal-based yoghurt, cereal-based juice, cereal-based wine, cereal-based coffee, freeze-dried cereal yoghurt blocks, etc.

Additionally or alternatively, the cereal-based product may be used as a dietary supplement or an additive. The dietary supplement may be used to supplement nutrients for humans and/or animals. The additive refers to a substance that is added to food or drink for animals or humans. When used as an additive, the cereal-based product may be used for producing cereal-based ice-cream, food paste, gruel, yogurt, milkshakes, bars, cookies, etc. The cereal-based product may also be used as an animal feed, such as cat food, dog food, etc.

The cereal-based product may be in the form of a suspension, powder, granules, sheets, blocks, etc. Different forms of the cereal-based product may be obtained with different processes on the treated mixture.

According to yet another aspect of the present disclosure, a use of an enzyme composition for preparing a cereal-based product from a cereal material is provided. The enzyme composition may include at least one malto-oligosaccharide forming amylase (MFAse). In some embodiments, preparing the cereal-based product may include i) providing a cereal mixture including the cereal material and an aqueous medium; ii) treating the cereal mixture with an effective amount of the enzyme composition under a temperature to obtain a treated mixture; and iii) processing the treated mixture from step ii) to obtain the cereal-based product. Details regarding the enzyme composition and the process of preparing the cereal-based product can be found elsewhere in the present disclosure, which is not repeated herein.

The present disclosure is further described according to the following examples, which should not be construed as limiting the scope of the present disclosure.

EXAMPLES

Example 1 Treating Raw Oats using G2-amylase

Raw oats were mixed in water at a concentration of about 5 to 15% (w/v) and cooked for 30 minutes. The oats were gelatinized after cooking. The gelatinized oats were wet-milled at a temperature of about 50° C. to 60° C. An enzyme preparation containing a G2-amylase, e.g. Novamyl 1000BG (Sigma A2986), was added to a cereal slurry (i.e., the wet-milled oats) at a dosage of 1.0 g per kg of oats. The reaction was conducted at a temperature of about 60° C. for 1-2 hours or until the viscosity of a suspension (i.e., the reacted cereal slurry) dropped to about 20 to 40 mPa·s at a shear rate of about 700 per second. The suspension was then heated to about 95° C. for 5 minutes to inactivate the G2-amylase.

After heating at about 95° C. for 5 minutes, the resultant suspension was analyzed by using High-Performance Liquid Chromatography (HPLC). The suspension was centrifuged at 16000 g to remove the insoluble substance, and a supernatant of the suspension was obtained. The supernatant containing soluble sugars were conducted for high-resolution oligosaccharide analysis using HPLC equipped with Bio-Rad Aminex HPX-42A column (Eluant: H2O; Flow rate: 0.6 mL/min; Temperature: 85° C.; Detection: RI).

Figure 1:
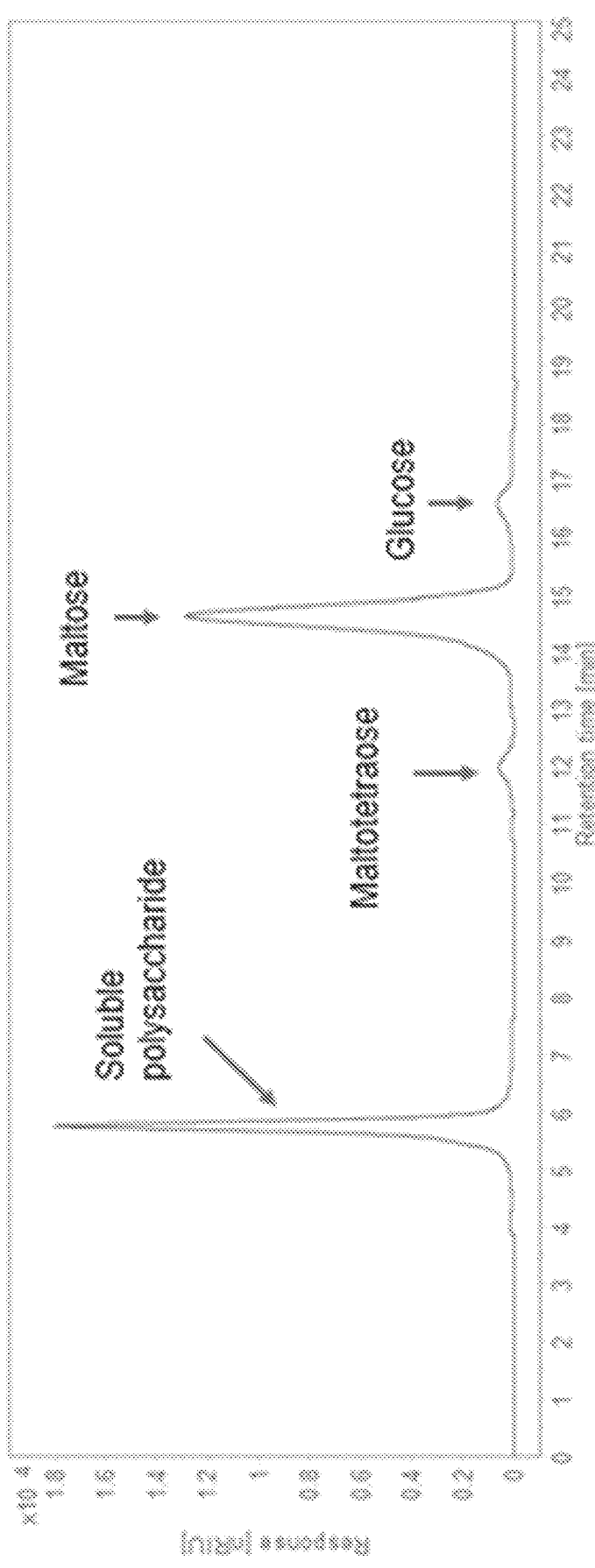
FIG. 1 is an analytical graph illustrating a result of soluble carbohydrate analysis of a cereal suspension treated by a G2-amylase according to some embodiments of the present disclosure.

The soluble carbohydrate of the suspension was analyzed. FIG. 1 is an analytical graph illustrating a result of soluble carbohydrate analysis of the suspension treated by the G2-amylase. As seen from FIG. 1, the suspension mainly included a substantial amount of soluble polysaccharide and malto-oligosaccharides, and little amount of glucose. The malto-oligosaccharides included mainly maltose and a little amount of other malto-oligosaccharides (e.g., maltotetraose). The content of the soluble polysaccharide was 21.8 g/L. The content of the maltotetraose was 1.0 g/L. The content of the maltose was 28.7 g/L. The content of the glucose was 1.1 g/L. The soluble polysaccharide included intact beta-glucan from the raw oat and maltodextrins generated from the reactions.

Example 2 Treating Raw Oats using G4-amylase

Raw oats were mixed, gelatinized, and milled as in Example 1. An enzyme preparation containing a G4-amylase, e.g. POWERFresh 3000 (Danisco, Copenhagen, Denmark), was added to a cereal slurry (i.e., the wet-milled oats) at a dosage of 1.0 g per kg of oats. The reaction was conducted at a temperature of about 60° C. for 1-2 hours or until the viscosity of a suspension (i.e., the reacted cereal slurry) dropped to about 20 to 40 mPa·s at a shear rate of about 700 per second. Finally, the suspension was heated as in Example 1. The heated suspension was analyzed by using HPLC as described in Example 1.

Figure 2:
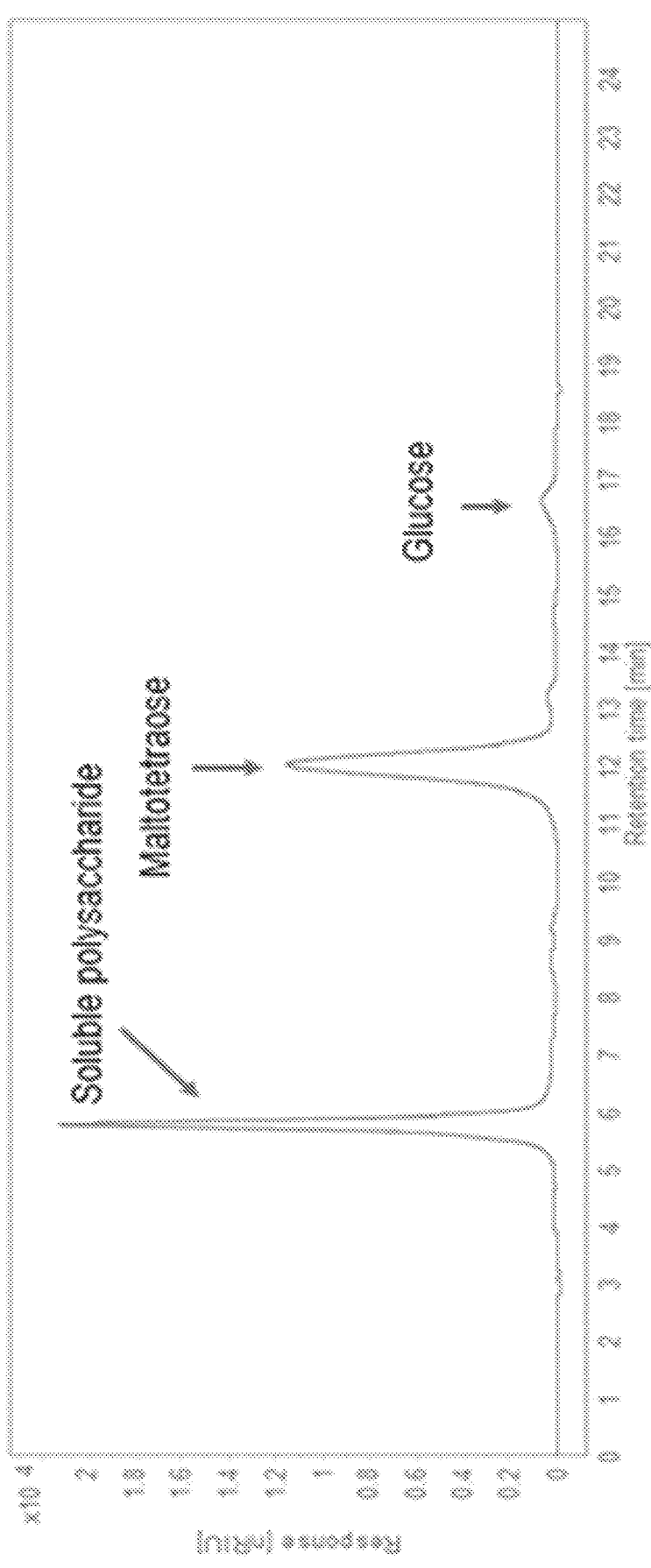
FIG. 2 is an analytical graph illustrating a result of soluble carbohydrate analysis of a cereal suspension treated by a G4-amylase according to some embodiments of the present disclosure.

FIG. 2 was an analytical graph illustrating a result of soluble carbohydrate analysis of the suspension treated by the G4-amylase. As seen from FIG. 2, the soluble carbohydrate of the suspension was measured. The suspension modified by the G4-amylase mainly included a substantial amount of soluble polysaccharide and malto-oligosaccharide, and little amount of glucose. The malto-oligosaccharide mainly included maltotetraose. The content of the soluble polysaccharide was 23.2 g/L. The content of the maltotetraose was 27 g/L. The content of the glucose was 1.4 g/L.

Example 3 Treating Raw Oats using G6-amylase

Raw oats were mixed, gelatinized, and milled as in Example 1. An enzyme preparation containing a G6-amylase, e.g. the E. coli expressed G6-amylase originating from Aerobacter aerogenes, was added to a cereal slurry (i.e., the wet-milled oats) at a dosage of 1.0 g per kg of oats. The reaction was conducted at a temperature of about 60° C. for 1-2 hours or until the viscosity of the suspension (i.e., the reacted cereal slurry) dropped to about 20 to 40 m·Pas at a shear rate of about 700 per second. Finally, the suspension was heated as in Example 1. The heated suspension was analyzed by using HPLC as described in Example 1.

FIG. 3 is an analytical graph illustrating a result of soluble carbohydrate analysis of the suspension treated by the G6-amylase. As seen from FIG. 3, the soluble carbohydrate of the suspension was measured. The suspension modified by the G6-amylase mainly included a substantial amount of soluble polysaccharide, various malto-oligosaccharides, and little amount of glucose. The malto-oligosaccharides mainly included maltose, maltotriose, maltotetraose, maltopentaose, and maltohexaose. The content of the soluble polysaccharide was 13.6 g/L. The contents of the maltose, maltotriose, maltotetraose, maltopentaose, and maltohexaose are 3.9 g/L, 4.7 g/L, 1.8 g/L, 2.0 g/L, 9.8 g/L, respectively. The content of the glucose was 1.3 g/L. Among the malto-oligosaccharides, the maltohexaose was the major malto-oligosaccharide, the content of which was highest.

Example 4 Treating Pea Starch using G4-amylase

Pea starch was mixed in water at a concentration of about 5 to 15% (w/v), and cooked for 30 minutes. After the temperature reduced to about 60° C., an enzyme preparation containing a G4-amylase, e.g. POWERFresh 3000 (Danisco, Copenhagen, Denmark), was added to the starch slurry at a dosage of 1.0 g per kg of the pea starch. The reaction was conducted at a temperature of about 60° C. for 1-2 hours or until the viscosity of a suspension (i.e., the reacted cereal slurry) dropped to about 20 to 40 m·Pa s at a shear rate of about 700 per second. Finally, the suspension was heated as in Example 1. The heated suspension was analyzed by using HPLC as described in Example 1.

FIG. 4 is an analytical graph illustrating a result of soluble carbohydrate analysis of the suspension treated by the G4-amylase. As seen from FIG. 4, the soluble carbohydrate of the suspension of the pea starch was measured. The suspension modified by the G4-amylase mainly included a substantial amount of soluble polysaccharide and malto-oligosaccharides. The malto-oligosaccharides mainly included maltose, maltotriose, and maltotetraose. The content of the soluble polysaccharide was 18.6 g/L. The contents of the maltose, maltotriose, and maltotetraose were 0.2 g/L, 1.1 g/L, and 41 g/L, respectively. Among the malto-oligosaccharides, the content of the maltotetraose was highest.

Example 5 Treating Raw Oats using Different Dosages of G4-amylase

Raw oats were mixed, gelatinized, and milled as in Example 1. An enzyme preparation containing a G4-amylase, e.g. POWERFresh 3000 (Danisco, Copenhagen, Denmark), was added to the cereal slurry at a dosage of 0.1, 0.2, or 1.0 g per kg of oats (i.e., the dosage is 0.01%, 0.02%, and 0.1%). The reaction was conducted at a temperature of about 60° C. for 1 hour. After heating at 95° C. for 5 minutes, the suspensions with different dosages were analyzed as in Example 1.

FIG. 5 is an analytical graph illustrating a result of soluble carbohydrate analysis of the suspensions treated by different dosages of the G4-amylase. As seen from FIG. 5, the soluble carbohydrates produced during the reactions were measured. The suspensions mainly included soluble polysaccharides and maltotetraoses. For the 0.01% of the G4-amylase, the contents of the soluble polysaccharide and the maltotetraose were 22.7 g/L and 1.9 g/L. For the 0.02% of the G4-amylase, the contents of the soluble polysaccharide and the maltotetraose were 20.1 g/L and 4.0 g/L. For the 0.1% of the G4-amylase, the contents of the soluble polysaccharide and the maltotetraose were 30.3 g/L and 14.6 g/L. With the dosages of the G4-amylase increased, the production of maltotetraose increased significantly, but not glucose, maltose, and other malto-oligosaccharides.

Example 6 Treating Raw Oats using G4-amylase for Different Reaction Time Periods Raw oats were mixed, gelatinized, and milled as in Example 1. An enzyme preparation containing a G4-amylase, e.g. POWERFresh 3000 (Danisco, Copenhagen, Denmark), was added to the cereal slurry at a dosage of 1.0 g per kg of oats. The reaction was conducted at a temperature of about 60° C. for 15 minutes, 45 minutes, and 2 hours. After heating at 95° C. for 5 minutes, the suspensions with different reaction times were analyzed as in Example 1.

FIG. 6 is an analytical graph illustrating a result of soluble carbohydrate analysis of the suspensions treated by the G4-amylase for different reaction time. As seen from FIG. 6, the suspensions mainly included soluble polysaccharides and maltotetraose. For the reaction time of 15 min, the contents of the soluble polysaccharide and the maltotetraose were 37 g/L and 11.8 g/L. For the reaction time of 45 min, the contents of the soluble polysaccharide and the maltotetraose were 28.7 g/L and 13.4 g/L. For the reaction time of 120 min, the contents of the soluble polysaccharide and the maltotetraose were 24.4 g/L and 20.8 g/L. With the reaction time increased, the production of maltotetraose increased significantly, but not glucose, maltose, and other malto-oligosaccharides.

Example 7 Treating Raw Oats using G4-amylase at Different Temperatures

Raw oats were mixed, gelatinized, and milled as in Example 1. An enzyme preparation containing a G4-amylase, e.g. POWERFresh 3000 (Danisco, Copenhagen, Denmark), was added to the cereal slurry at a dosage of about 2.0 g per kg of oats. The reaction was conducted at a temperature of 40° C., 60° C., and 75° C. for 1 hour. After heating at 95° C. for 5 minutes, the suspensions with different reaction temperatures were analyzed as in Example 1.

FIG. 7 is an analytical graph illustrating a result of soluble carbohydrate analysis of the suspensions treated by the G4-amylase at different reaction temperatures. As seen from FIG. 7, the suspensions mainly included soluble polysaccharides and maltotetraose. For the reaction temperature at 40° C., the contents of the soluble polysaccharide and the maltotetraose were 22.9 g/L and 30.8 g/L. For the reaction temperature at 60° C., the contents of the soluble polysaccharide and the maltotetraose were 23.1 g/L and 34.7 g/L. For the reaction temperature at 75° C., the contents of the soluble polysaccharide and the maltotetraose were 28.2 g/L and 35.5 g/L. The enzyme remained good activities at all the temperatures tested here. With the reaction temperature increased, the amount of produced soluble polysaccharides and maltotetraose slightly increased.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer-readable medium having computer readable program code embodied thereon.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method of preparing a cereal-based product, comprising:

i) providing a cereal mixture including a cereal material and an aqueous medium by: mixing raw oats in water at a concentration in a range of 5 to 15% (w/v), cooking the raw oats and the water, gelatinizing the raw oats after cooking, and wet-milling the gelatinized raw oats at a temperature in a range of 50° C. to 60° C.;

ii) treating the cereal mixture with an effective amount of an enzyme composition under a temperature to obtain a treated mixture, the enzyme composition including at least one malto-oligosaccharide forming amylase (MFAse), wherein the at least one MFAse is a malto-tetraose-forming amylase (G4-amylase), and the effective amount of the enzyme composition is 1% of the raw oats by weight; and iii) processing the treated mixture from step ii) to obtain the cereal-based product, wherein the cereal-based product is a cereal suspension, a proportion of glucose in total soluble sugar in the cereal-based product is less than 5% by weight and a maltotetraose in the total soluble sugar in the cereal-based product is more than 50% by weight.

2. The method of claim 1, wherein the temperature of step (ii) is in a range of 40° C. to 75° C.

3. The method of claim 1, wherein the temperature of step is about 60° C.

4. The method of claim 1, wherein a termination condition for step (ii) includes at least one of:

a time period for treating the cereal mixture using the effective amount of the enzyme composition exceeds a time threshold;

a viscosity of the cereal mixture is less than a viscosity threshold; or a starch level in the cereal mixture is less than a starch level threshold.

5. The method of claim 4, wherein the viscosity threshold of the cereal mixture is 80 mPa·s at a shear rate of about 700 per second.

6. The method of claim 4, wherein the starch level threshold is 60% of an original starch level in the cereal mixture.

7. The method of claim 1, wherein processing the treated mixture further includes at least one of: a homogenizing process, a sterilization process, a refrigeration process, a concentrating process, a filtering process, or a drying process.

8. A cereal-based product prepared by the method of claim 1.

9. The cereal-based product of claim 8, comprising malto-oligosaccharides and maltodextrin units.

10. The cereal-based product of claim 8, wherein a substantial amount of β-glucans and proteins included in the cereal material is retained in the cereal-based product.

11. The cereal-based product of claim 8, wherein a proportion of glucose in total soluble sugar in the cereal-based product is less than 3% of the cereal-based product by weight.

12. The cereal-based product of claim 8, wherein the cereal-based product is used as a food, a drink, an animal feed, a dietary supplement, or an additive.

13. The method of claim 3, wherein step (ii) is performed for one to two hours.

14. The method of claim 1, wherein step ii) is terminated when a viscosity of a suspension drops to below a viscosity threshold, the viscosity threshold being in a range of 20 to 40 mPa·s at a shear rate of about 700 per second.

15. The method of claim 1, wherein the proportion of glucose in total soluble sugar in the cereal-based product is less than 3% by weight.

* * * * *